United States Patent [19]

Abdulla

[11] 4,075,000
[45] Feb. 21, 1978

[54] HERBICIDAL USE OF 4-AMINO-3,3-DIMETHYL-1-PHENYL-2-AZETIDINONES

[75] Inventor: Riaz F. Abdulla, Greenfield, Ind.

[73] Assignee: Eli Lilly and Company, Indianapolis, Ind.

[21] Appl. No.: 581,017

[22] Filed: May 27, 1975

[51] Int. Cl.$^2$ ............................................. A01N 9/22
[52] U.S. Cl. .................................. 71/88; 260/239 A; 544/111
[58] Field of Search .......................................... 71/88

[56] References Cited

U.S. PATENT DOCUMENTS

| | | | |
|---|---|---|---|
| 3,194,801 | 7/1965 | Perelman | 260/239 |
| 3,958,974 | 5/1976 | Hotz et al. | 71/88 |

*Primary Examiner*—Lewis Gotts
*Assistant Examiner*—Catherine L. Mills
*Attorney, Agent, or Firm*—William E. Maycock; Joseph A. Jones; Everet F. Smith

[57] ABSTRACT

A class of 4-amino-3,3-dimethyl-1-phenyl-2-azetidinones reduce the vigor of unwanted herbaceous plants to which the compounds are applied. The compounds are effective when applied either preemergence or postemergence at rates from about 2 to about 20 kg./ha.

7 Claims, No Drawings

4,075,000

HERBICIDAL USE OF 4-AMINO-3,3-DIMETHYL-1-PHENYL-2-AZETIDINONES

BACKGROUND OF THE INVENTION

This invention belongs to the field of agricultural chemistry, and provides to the art a new method of reducing the vigor of unwanted plants. It is well known that the growth of plants out of place has extremely deleterious effects on the crops which are infested with the unwanted plants. Unwanted plants growing in cropland, as well as in fallow land or in land intended to be kept permanently bare, consume soil nutrients and water. Thus, such plants constitute a serious drain on the resources of the soil. When growing in cropland, such plants also shade the crop plants from the sun.

Compounds such as are used in this invention have not previously been known to be useful agricultural chemicals. The closest known related herbicidal compounds are the uretidin-2,4-diones of Belgian Pat. No. 768,051.

The compounds used in this invention were disclosed by Perelman, U.S. Pat. No. 3,194,801, who stated that the compounds have effects on the central nervous system. Related compounds have recently been disclosed to have enzymatic activities, U.S. Pat. No. 3,816,408. Further β-lactam compounds, somewhat related to those of the present invention, were discussed as antibiotics by Bose et al., J. Med. Chem. 17, 541–44 (1974).

SUMMARY OF THE INVENTION

The vigor of unwanted herbaceous plants is reduced by contacting the plants with an herbicidally-effective amount of a compound of the formula

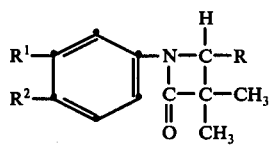

wherein
R represents
  dimethylamino,
  diethylamino, or
  morpholino;
$R^1$ and $R^2$ independently represent
  hydrogen,
  methyl,
  chloro,
  fluoro,
  methoxy,
  methylthio, or
  trifluoromethyl;
provided that both $R^1$ and $R^2$ do not represent hydrogen, and that neither $R^1$ nor $R^2$ represents hydrogen when R represents morpholino.

DESCRIPTION OF THE PREFERRED EMBODIMENT

The following compounds of this invention are presented to assure that those of skill in the art understand the invention. The compounds below do not, of course, bound the invention, but are merely exemplary of it.
3,3-dimethyl-4-morpholino-1-(3,4-xylyl)-2-azetidinone
1-(4-chloro-m-tolyl)-3,3-dimethyl-4-morpholino-2-azetidinone
3,3-dimethyl-1-(3-fluoro-4-methoxyphenyl)-4-morpholino-2-azetidinone
3,3-dimethyl-1-(3-methoxy-α,α,α-trifluoro-p-tolyl)-4-morpholino-2-azetidinone
1-(4-chloro-α,α,α-trifluoro-m-tolyl)-3,3-dimethyl-4-morpholino-2-azetidinone
1-(3,4-difluorophenyl)-3,3-dimethyl-4-morpholino-2-azetidinone
3,3-dimethyl-1-(4-fluoro-3-methylthiophenyl)-4-morpholino-2-azetidinone
3,3-dimethyl-1-(4-methylthio-m-tolyl)-4-morpholino-2-azetidinone
3,3-dimethyl-4-diethylamino-1-(α,α,α-trifluoro-m-tolyl)-2-azetidinone
3,3-dimethyl-4-dimethylamino-1-(4-fluoro-m-tolyl)-2-azetidinone
1-(4-chlorophenyl)-3,3-dimethyl-4-dimethylamino-2-azetidinone
1-(3-chloro-p-tolyl)-3,3-dimethyl-4-dimethylamino-2-azetidinone
1-(3,4-dimethoxyphenyl)-3,3-dimethyl-4-dimethylamino-2-azetidinone
3,3-dimethyl-4-dimethylamino-1-(3-fluorophenyl)-2-azetidinone
3,3-dimethyl-4-dimethylamino-1-(3,4-dimethylthiophenyl)-2-azetidinone
3,3-dimethyl-4-dimethylamino-1-(α,α,α-trifluoro-p-tolyl)-2-azetidinone
4-diethylamino-3,3-dimethyl-1-(4-methoxyphenyl)-2-azetidinone
4-diethylamino-3,3-dimethyl-1-(3-trifluoromethyl-p-tolyl)-2-azetidinone
1-(3-chlorophenyl)-4-diethylamino-3,3-dimethyl-2-azetidinone
4-diethylamino-3,3-dimethyl-1-(m-tolyl)-2-azetidinone
4-diethylamino-3,3-dimethyl-1-(3,4-difluorophenyl)-2-azetidinone
4-diethylamino-3,3-dimethyl-1-(3,4-dimethylthiophenyl)-2-azetidinone
1-(4-chloro-3-methoxyphenyl)-4-diethylamino-3,3-dimethyl-2-azetidinone
4-diethylamino-3,3-dimethyl-1-(α,α,α,3-tetrafluoro-p-tolyl)-2-azetidinone The synthesis of the compounds used in this invention was taught by Perelman, U.S. Pat. No. 3,194,801, the specification of which is herein incorporated by reference. A description of the synthesis will be given here, however, for the convenience of the reader. The compounds are prepared by reacting a substituted-phenylisocyanate with an enamine, which is prepared by the reaction of isobutyraldehyde with dimethylamine, diethylamine or morpholine. Brief reaction times at temperatures in the range of 20°–100° C. are used. No solvent is needed in the reaction mixture. The reaction is exothermic, but it is frequently necessary to heat the reaction mixture to about 50° C. to initiate the reaction, and then to cool the reaction mixture to keep the temperature in the desired range. The following preparative example illustrates the synthetic process.

EXAMPLE 1

1-(3,4-dichlorophenyl)-3,3-dimethyl-4-morpholino-2-azetidinone

A 1.88 g. portion of 3,4-dichlorophenylisocyanate was added to 2.82 g. of 1-morpholino-1-isobutene. The mixture was stirred at room temperature for 48 hours. At the end of that time, the excess enamine was removed under vacuum, and the remaining oil, 3.0 g., was found by nuclear magnetic resonance analysis to be 1-(3,4-dichlorophenyl)-3,3-dimethyl-4-morpholino-2-azetidinone, a liquid.

The above general procedure, as illustrated by the above synthetic example, is used to make all of the other compounds useful in this invention, such as the following.

EXAMPLE 2

3,3-dimethyl-4-dimethylamino-1-(m-tolyl)-2-azetidinone, b.p. 70° C. dec.

EXAMPLE 3

1-(3-chlorophenyl)-3,3-dimethyl-4-dimethylamino-2-azetidinone, liquid

EXAMPLE 4

3,3-dimethyl-4-dimethylamino-1-($\alpha,\alpha,\alpha$-trifluoro-m-tolyl)-2-azetidinone, liquid

EXAMPLE 5

1-(3-chloro-p-tolyl)-3,3-dimethyl-4-morpholino-2-azetidinone, glass

EXAMPLE 6

3,3-dimethyl-4-dimethylamino-1-(3-methoxyphenyl)-2-azetidinone, liquid

EXAMPLE 7

3,3-dimethyl-4-dimethylamino-1-(4-methoxyphenyl)-2-azetidinone, liquid

EXAMPLE 8

3,3-dimethyl-4-dimethylamino-1-(3,4-xylyl)-2-azetidinone, liquid

EXAMPLE 9

3,3-dimethyl-4-dimethylamino-1-(4-methylthiophenyl)-2-azetidinone, liquid

The compounds described above have been tested in a number of herbicidal test systems to determine the range of their herbicidal efficacy. The results produced by the compounds in the representative tests reported below are exemplary of the activity of the compounds.

Compound application rates are expressed in kilograms of the compound per hectare of land (kg./ha.) throughout this specification and claims. Blank spaces in the tables below indicate that the compound was not tested against the named species. In the tests below, plants were rated on a 1-5 scale, on which 1 indicates normal plants and 5 indicates dead plants or no emergence.

Test 1 broad spectrum greenhouse test

Square plastic pots were filled with a sandy sterilized greenhouse soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone: ethanol at the rate of 2 g. per 100 ml. The solution also contained about 2 g. per 100 ml. of an anionic--nonionic surfactant blend. One ml. of the solution was diluted to 4 ml. with deionized water, and 1-½ ml. of the resulting solution was applied to each pot, resulting in an application rate of 16.8 kg./ha. of test compound.

After the compounds were applied, the pots were moved to the greenhouse, watered as necessary, and observed and rated about 10–13 days after application of the compounds. Untreated control plants were used as standards in every test.

The table below reports results of testing typical compounds of the invention. The compounds are identified by their example numbers above.

| Compound of Example No. | Preemergence | | | Postemergence | | |
|---|---|---|---|---|---|---|
| | Tomato | Large Crabgrass | Pigweed | Tomato | Large Crabgrass | Pigweed |
| 1 | 4 | 4 | 3 | 5 | 2 | 2 |
| 2 | 5 | 3 | 4 | 5 | 4 | 5 |
| 3 | 5 | 3 | 4 | 5 | 4 | 5 |
| 4 | 3 | 3 | 3 | 5 | 3 | 4 |
| 5 | 2 | 2 | 1 | 2 | 1 | 1 |
| 6 | 3 | 3 | 3 | 5 | 4 | 5 |
| 7 | 3 | 2 | 3 | 3 | 1 | 3 |
| 8 | 5 | 4 | 4 | 5 | 3 | 4 |
| 9 | 2 | 2 | 2 | 3 | 2 | 2 |

Test 2 seven-species greenhouse test

The test was conducted in general like the test above. The seeds were planted in flat metal trays, rather than in pots. The compounds were formulated according to the procedure above, except that about 6 g./100 ml. of the compound was dissolved in the surfactant-containing solvent, and about 1 part of the organic solution was diluted with 12 parts of water before application to the trays. The compounds were applied at the rate of 9.0 kg./ha., and at lower rates in some instances as shown below, and the results of testing against the species named below were as follows.

| Compound of Exam. No. | Rate of Appln. kg./ha. | Preemergence | | | | | | | Postemergence | | | | | | |
|---|---|---|---|---|---|---|---|---|---|---|---|---|---|---|---|
| | | corn | Large Crabgrass | Pigweed | Foxtail | Velvet leaf | Morning Glory | Zinnia | corn | Large Crabgrass | Pigweed | Foxtail | Velvet leaf | Morning Glory | Zinnia |
| 1 | 9.0 | 1 | 1 | 1 | 1 | 1 | 1 | 1 | 2 | 2 | 3 | 3 | 2 | 2 | 3 |
| 2 | 9.0 | 1 | 3 | 2 | 2 | 2 | 1 | 1 | 2 | 3 | 4 | 3 | 4 | 3 | 3 |
|   | 4.5 |   |   |   |   |   |   |   | 2 | 4 | 4 | 3 | 4 | 4 | 4 |
|   | 2.2 |   |   |   |   |   |   |   | 1 | 3 | 3 | 2 | 3 | 2 | 2 |
|   | 1.1 |   |   |   |   |   |   |   | 1 | 2 | 2 | 2 | 1 | 2 | 2 |
| 3 | 9.0 | 1 | 3 | 3 | 2 | 1 | 1 | 2 | 2 | 3 | 4 | 4 | 4 | 3 | 4 |
|   | 4.5 |   |   |   |   |   |   |   | 2 | 3 | 4 | 2 | 3 | 3 | 3 |
|   | 2.2 |   |   |   |   |   |   |   | 2 | 2 | 3 | 2 | 2 | 2 | 2 |

| | | Preemergence | | | | | | | Postemergence | | | | | | |
|---|---|---|---|---|---|---|---|---|---|---|---|---|---|---|---|
| Compound of Exam. No. | Rate of Appln. kg./ha. | corn | Large Crab-grass | Pigweed | Fox-tail | Velvet leaf | Morn-ing Glory | Zinnia | corn | Large Crab-grass | Pigweed | Fox-tail | Velvet leaf | Morn-ing Glory | Zinnia |
| | 1.1 | | | | | | | | 1 | 2 | 2 | 2 | 2 | 2 | 2 |
| 4 | 9.0 | 1 | 3 | 3 | 2 | 2 | 1 | 1 | 2 | 4 | 3 | 4 | 3 | 3 | 3 |
| | 4.5 | | | | | | | | 1 | 3 | 4 | 3 | 3 | 3 | 3 |
| | 2.2 | | | | | | | | 1 | 2 | 3 | 2 | 2 | 3 | 2 |
| | 1.1 | | | | | | | | 1 | 2 | 2 | 2 | 2 | 2 | 2 |
| 5 | 9.0 | 1 | 1 | 1 | 1 | 1 | 1 | 1 | 1 | 2 | 1 | 3 | 2 | 1 | 1 |
| 6 | 9.0 | 1 | 2 | 3 | 3 | 3 | 2 | 2 | 1 | 2 | 3 | 3 | 3 | 2 | 2 |
| 7 | 9.0 | 1 | 2 | 2 | 2 | 2 | 1 | | 1 | 2 | 4 | 2 | 3 | 3 | 3 |
| 8 | 9.0 | 1 | 1 | 1 | 1 | 1 | 1 | 1 | 1 | 3 | 2 | 2 | 3 | 1 | 2 |
| 9 | 9.0 | 1 | 1 | 1 | 1 | 1 | 1 | 1 | 2 | 2 | 3 | 3 | 3 | 3 | 3 |

The compounds of Examples 2 and 3 were also tested in a greenhouse test against broadleaf weeds which are resistant to many classes of herbicides. The compounds were applied preemergence at 9.0 kg./ha. to nightshade, sicklepod and prickly sida. The compound of Example 2 completely killed the population of sicklepod and prickly sida, and was given a rating of 4 against nightshade. The other compound gave control rated at 4 against sicklepod and prickly sida and control rated at 3 against nightshade.

The broad-spectrum activity of the compounds of this invention is clearly illustrated by the above examples. The test results point up the efficacy of the compounds against annual grasses, the relatively easily-controlled broadleaves such as pigweed, and the more resistant broadleaves such as nightshade. Plant scientists will recognize that the exemplified activity of the compounds shows that the compounds are broadly effective against herbaceous weeds.

As the above test results demonstrate, this invention is a method of reducing the vigor of unwanted herbaceous plants which comprises contacting the plants with an herbicidally-effective amount of one of the compounds described above. In some instances, as is clear from the test results, the whole population of the contacted plant is killed. In other instances, part of the plants are killed and part of them are injured, and in still other instances, none of the plants are killed but are merely injured by application of the compound. It will be understood that reducing the vigor of the unwanted plant population by injuring the individual plants, or by killing part and injuring part, is beneficial even though some part of the plant population survives application of the compound. The plants, the vigor of which has been reduced, are unusually susceptible to the stresses, such as disease, drought, lack of nutrients and so forth, which normally afflict plants.

Thus, the treated plants, even though they survive application of the compound, are likely to expire due to stress of the environment. Further, if the treated plants are growing in cropland, the crop, growing normally, tends to shade out the treated plants of reduced vigor. The crop, therefore, has a great advantage over the treated unwanted plants in the competition for nutrients and sunlight. Still further, when the treated plants are growing in fallow land, or industrial property which is desired to be bare, the fact that their vigor is reduced necessarily tends to minimize the treated plants' consumption of water and nutrients, and also minimizes the fire hazard and nuisance which the plants present.

The compounds are herbicidally effective when applied both preemergence and postemergence. Thus, they can be applied to the soil to kill and injure weeds by soil contact when the weed seeds are germinating and emerging, and can also be used to kill and injure growing weeds by direct contact with the exposed portions of the weeds. Postemergence application of the compounds, wherein the unwanted herbaceous plants are directly contacted with the compound, is preferred.

The compounds with which the method of this invention is preferably carried out are 3,3-dimethyl-4-dimethylamino-1-(3-methoxyphenyl)-2-azetidinone, 3,3-dimethyl-4-dimethylamino-1-(m-tolyl)-2-azetidinone, 3,3-dimethyl-4-dimethylamino-1-($\alpha,\alpha,\alpha$-trifluoro-m-tolyl)-2-azetidinone, 1-(3-chlorophenyl)-3,3-dimethyl-4-dimethylamino-2-azetidinone, and 3,3-dimethyl-4-dimethylamino-1-(3,4-xylyl)-2-azetidinone.

The best application rate of a given compound of the invention for the control of a given weed varies, of course, depending upon the climate, soil type, water and organic matter contents of the soil and other factors known to those skilled in plant science. It will be found, however, that the optimum application rate is usually in the range from about 2.0 to about 20 kg./ha.

The compounds are applied to the soil or to emerged weeds in the manners usual in agriculture. They may be applied to the soil in the form of either water-dispersed or granular formulations, the preparation of which will be discussed below. Usually, water-dispersed formulations will be used for the application of the compounds to emerged weeds. The formulations are applied with any of the many types of sprayers and granular applicators which are in wide use for the distribution of agricultural chemicals over soil or standing vegetation.

The compounds are normally used in the practice of this invention in the form of herbicidal compositions which are an important embodiment of the invention. An herbicidal composition of this invention comprises a compound of the invention and an inert carrier. In general, the compositions are formulated in the manners usual in agricultural chemistry, and are novel only because of the vital presence of the herbicidal compound.

Very often, the compounds are formulated as concentrated compositions which are applied either to the soil or the foliage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier and surfactants. The concentration of the compound is usually from about 10 percent to about 90 percent. The inert carrier is usually chosen from among the attapulgite clays, the montmorillonite clays, the diatomaceous earths and the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

It has become customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematicides and other herbicides as may be desirable and convenient.

I claim:

1. A method of reducing the vigor of unwanted herbaceous plants which comprises contacting the plants with an herbicidally-effective amount of a compound of the formula

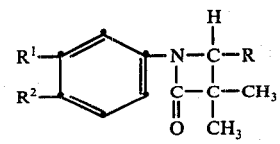

wherein
R represents
dimethylamino,
diethylamino, or
morpholino;
$R^1$ and $R^2$ independently represent
hydrogen,
methyl,
chloro,
fluoro,
methoxy,
methylthio, or
trifluoromethyl;
provided that both $R^1$ and $R^2$ do not represent hydrogen, and that neither $R^1$ nor $R^2$ represents hydrogen when R represents morpholino.

2. A method of claim 1 wherein the amount of the compound is from about 2 to about 20 kg./ha.

3. The method of claim 2 wherein the compound is 3,3-dimethyl-4-dimethylamino-1-(3-methoxyphenyl)-2-azetidinone.

4. The method of claim 2 wherein the compound is 3,3-dimethyl-4-dimethylamino-1-(m-tolyl)-2-azetidinone.

5. The method of claim 2 wherein the compound is 3,3-dimethyl-4-dimethylamino-1-(α,α,α-trifluoro-m-tolyl)-2-azetidinone.

6. The method of claim 2 wherein the compound is 1-(3-chlorophenyl)-3,3-dimethyl-4-dimethylamino-2-azetidinone.

7. The method of claim 2 wherein the compound is 3,3-dimethyl-4-dimethylamino-1-(3,4-xylyl)-2-azetidinone.

* * * * *